US008900692B2

(12) United States Patent
Shikinami

(10) Patent No.: US 8,900,692 B2
(45) Date of Patent: Dec. 2, 2014

(54) REINFORCED COMPOSIT THAT IS COMPLEMENTARILY REINFORCED AND PRODUCTION METHOD THEREFOR

(76) Inventor: Yasuo Shikinami, Kusatsu (JP)

(*) Notice: Subject to any disclaimer, the term of this patent is extended or adjusted under 35 U.S.C. 154(b) by 0 days.

(21) Appl. No.: 13/811,174

(22) PCT Filed: Oct. 21, 2010

(86) PCT No.: PCT/JP2010/006249

§ 371 (c)(1),
(2), (4) Date: Apr. 10, 2013

(87) PCT Pub. No.: WO2012/053037

PCT Pub. Date: Apr. 26, 2012

(65) Prior Publication Data

US 2013/0209765 A1     Aug. 15, 2013

(51) Int. Cl.
*B32B 5/26*     (2006.01)
*A61L 27/46*     (2006.01)
(Continued)

(52) U.S. Cl.
CPC . *B32B 5/26* (2013.01); *A61L 27/46* (2013.01); *B29C 43/003* (2013.01); *B29C 43/16* (2013.01); *B32B 5/022* (2013.01); *B32B 7/02* (2013.01); *D04H 1/559* (2013.01); *A61L 27/18* (2013.01); *A61L 27/56* (2013.01); *D04H 3/14* (2013.01); *B32B 5/08* (2013.01); *B29K 2067/046* (2013.01); *B29K 2105/0809* (2013.01); *A61L 2430/02* (2013.01)
USPC ............................ 428/215; 264/125; 442/381

(58) Field of Classification Search
CPC .................... A61F 2/2846; A61F 2002/30062; B29C 43/16; B32B 5/26; D04H 13/007; D04H 5/06; D04H 3/14; D04H 3/147; D04H 3/153
USPC ............................ 428/215; 264/125; 442/381
See application file for complete search history.

(56) References Cited

U.S. PATENT DOCUMENTS

| 2003/0006533 A1* | 1/2003 | Shikinami et al. | ............ 264/323 |
| 2007/0099524 A1* | 5/2007 | Porter | .............................. 442/38 |

(Continued)

FOREIGN PATENT DOCUMENTS

| JP | 8-134758 A | 5/1996 |
| JP | 9-234242 A | 9/1997 |

(Continued)

OTHER PUBLICATIONS

International Search Report for PCT/JP2010/006249, mailing date of Dec. 28, 2010.

*Primary Examiner* — Aaron Austin
*Assistant Examiner* — Jasper Saberi
(74) *Attorney, Agent, or Firm* — Westerman, Hattori, Daniels & Adrian, LLP

(57) ABSTRACT

The forging-reinforced composite constructed of a plurality of different kinds of materials, which have compatible polymers comprising crystalline and glass phases at room temperature for the matrices, is a composite, wherein, by being forged in a layer-separated state in which each of the different kinds of materials forms micron-sized fibrous layers that crossed and intermingled three-dimensionally with each other and the arrangement of the crystals in the crystalline phases configuring the matrices having a disordered orientation without anisotropy in a variety of directions, the inherent-properties of the material of each layer are complementarily reinforced. A mixed nonwoven fabric wherein microfibers are crossed and intermingled two- or three-dimensionally with each other is manufactured and heated under pressure at or above the melting point of the polymers to manufacture compact blocks wherein the microfibers are welded. Then, the compact blocks are forged at a crystallization temperature.

4 Claims, 1 Drawing Sheet

(51) Int. Cl.

| | |
|---|---|
| *B29C 43/00* | (2006.01) |
| *B29C 43/16* | (2006.01) |
| *B32B 5/02* | (2006.01) |
| *B32B 7/02* | (2006.01) |
| *D04H 1/559* | (2012.01) |
| *A61L 27/18* | (2006.01) |
| *A61L 27/56* | (2006.01) |
| *D04H 3/14* | (2012.01) |
| *B32B 5/08* | (2006.01) |
| *B29K 67/00* | (2006.01) |
| *B29K 105/08* | (2006.01) |

(56) References Cited

U.S. PATENT DOCUMENTS

| | | |
|---|---|---|
| 2008/0311343 A1 | 12/2008 | Kinn et al. |
| 2009/0012613 A1* | 1/2009 | Farnsworth et al. ....... 623/11.11 |
| 2009/0028921 A1* | 1/2009 | Arinzeh ...................... 424/423 |

FOREIGN PATENT DOCUMENTS

| | | |
|---|---|---|
| JP | 11-61615 A | 3/1999 |
| JP | 2000-84064 A | 3/2000 |
| JP | 3215047 B2 | 10/2001 |
| JP | 3418350 B2 | 6/2003 |
| JP | 2008-540864 A | 11/2008 |

* cited by examiner

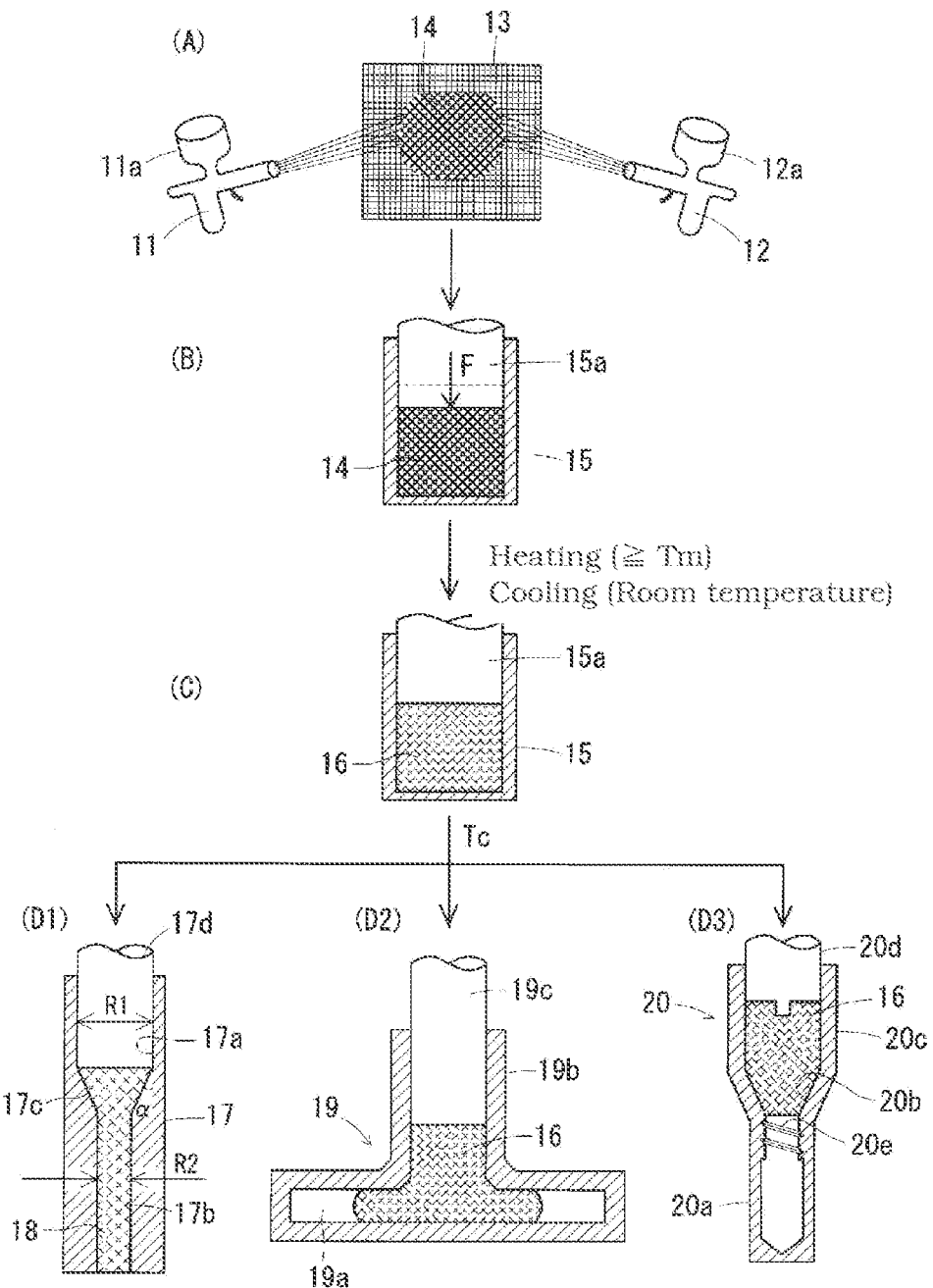

REINFORCED COMPOSIT THAT IS COMPLEMENTARILY REINFORCED AND PRODUCTION METHOD THEREFOR

TECHNICAL FIELD

The present invention relates to a novel reinforced composite of a mixture of a plural of hetero-componential, different kinds of, polymers which are essentially chemical compatible, and a production method thereof. More specifically, the present invention relates to a forging-reinforced composite comprising a composite which is composed of a plural of polymer materials containing, as a matrix, crystalline polymers (with crystalline and glass phases at room temperature) which are essentially chemical compatible and forged, and where each of the polymer materials forms a fibrous layer having a thickness of a micron meter (μm) order which is in the form of layer-separation, and those layers form a manner of organization where the layers are three-dimensionally crossed and intermingled with each other; and a production method thereof. The forging-reinforced composite of the present invention has various improved properties of toughness such as tenacity, ductility, extensibility and resistance to repetitive loading where one layer reinforces complementarily physical defects of the other layer and vise versa. The composite is an excellent material suitable to various toughness uses such as high strength medical bone fixation and joint devices.

BACKGROUND ARTS

Conventional reinforcing methods of organic polymer materials may be classified roughly to the followings.

[1] Case that there is No Compatibility Between Materials

1) Improvement by Mixing Fillers (Reinforcing Materials)

This method is used for solidifying by enveloping the fillers with a thermosetting resin. Generally, a reinforced composite having properties of the fillers is produced by charging the thermosetting resin before curing with fine particles of fillers which are inorganic materials or immiscible resins, and then curing the resin. In case that the fillers are simply mixed with the thermosetting resin without crosslinking or curing, however, since the resin matrix is diluted by the fillers to generate exfoliating of the resin from the fillers at their boundary surface, contrary to expectation, the strength is totally lowered in general and reinforcement of physical properties can not be expected. In order to improve the strength, it is essential to enhance the bonding force between both by applying some methods such as addition of bonding agents. In the field of medical materials, use of an unknown binder such as a coupling agent which is necessary to investigate its toxicity is not desired.

In view of the closest packing mechanism, in order to exhibit chemical, physiological properties of fillers sufficiently, it is necessary to fill with the fillers in an amount of more than 33.3. vol % which is an amount that the fillers exist continuously throughout a molded material from back side to front side. In case that a large amount of foreign materials are mixed and any binder is not used, it cannot be avoided that a certain kind of properties is remarkably lowered.

2) Improvement by Fiber Reinforcing

This reinforcing method is most effective and is most generally used. In this case, a matrix resin and fibers to reinforce have different natures and are immiscible to each other. The reason is that, when the fiber with the similar nature is added to a matrix resin which is dissolved in a solvent, or melted in a matrix, or in the form of solution such as monomer or oligomer, the fiber is dissolved in the matrix resin and then is destroyed its fibrous structure. High strength fibers such as carbon, glass, KEVLAR and boron are used for reinforcement, because these are essentially different from the matrix resin and cannot be dissolved therein. In medical devices, though there has been studied reinforcement by bioinert fibers or bioceramics fibers which are highly bio-compatible among those fillers, it is very afraid that there is a danger that such a fine fiber stimulates physically cells or organs. Examples of the bioinert fibers include non-biodegradable and non-bioabsorbable PEEK (polyether-ether-ketone), carbon fiber, and the like. A method where reinforcing by using the non-biodegradable and non-bioabsorbable fibers has not yet been clinically used, because those fiber fragments give undesired physical stimulation which is harmful to a living body.

A guidance of fiber reinforcement resistive to breakdown is not to use a strong fiber, but is to use a matrix resin which is tough and is hard to generate cracks, and to prevent exfoliating at the interface of the fiber and the resin. From this viewpoint, though it is one idea to reinforce by using a compatible fiber having same nature, considering the physical stimulation to a living body, it cannot be recommended to use a composite produced by this method as medical materials.

3) Reinforcement by Crystal Orientation

Conventionally, for reinforcing a crystalline polymer, there is employed a method where crystals are oriented in a certain determined direction in order to exhibit intermolecular force of adjacent polymer chains effectively. There is a special method where a film is reinforced by biaxial drawing, but a usual method is to enhance the intermolecular force by uniaxial drawing. In the uniaxial drawing, since the crystals are oriented in the uniaxially drawn direction, there happens anisotropy of strength due to the crystal orientation in the mechanical direction (MD) and the traverse direction (TD) at a right angle thereto. In a molded material that dislikes the anisotropy of strength, it is demanded a reinforcing method where an eccentric crystal orientation is avoided as possible. The press-forging method (Patent Document 1) invented to a poly (lactic acid) by the present inventor falls under this method, which could avoid significantly the anisotropy according to the conventional method by orienting in the multiaxial directions at certain gradient angles to the center axis along with MD.

The forging reinforcing method of Patent Document 1 is effectively applied basically to a crystalline polymer composed of a crystalline phase and a glass phase at a room temperature and has a glass transition temperature of a room temperature or higher, or a composite thereof and organic fine particles. Typical examples of the polymer composed of a glass phase and a crystalline phase at ordinary temperatures and having a glass transition point: Tg (° C.) of a room temperature or higher, and a melting point Tm (° C.) where the crystalline phase is molten are in the followings. Nylon 6 (Tg: 47° C., Tm: 255° C.), Nylon 66 (Tg: 49° C., Tm: 267° C.), polyethylene terephthalate (Tg: 68° C. and 81° C., Tm: 260° C.), polyvinyl chloride (Tg: 82° C., less crystalline phase, Tm: 180° C.), polystyrene (Tg: 100° C., Tm: 230° C.), polymethyl methacrylate (Tg: 70° C., Thermal deformation temperature: 140° C.), poly (lactic acid) (Tg: 65° C., Tm: 185° C.), and the like. Since these are not melted between Tg and Tm, but are convert to be softened in parallel with temperature elevation, plastic deformation can be carried out between Tg and Tm by the forging treatment if applying a pressure larger than that of the case of melt molding. In addition, since crystallization is progressed gradually between those temperatures, strength of material can be changed by varying crystallinity or varying the orientation of crystals. Of course, strength can be extremely increased by enhancing the orientation. By using this principle smartly, the present inventor has reinforced a poly (lactic acid) (PLLA) or a composite (HA/PLLA) of PLLA and hydroxyapatite (HA) fine particles by subjecting to crystal orientation by forging. These forging-reinforced products are now used clinically as a high strength, bio-active, biodegradable bone fixation and joint devices.

The present inventor has also invented a method where the anisotropic mechanical strength is further improved by subjecting the once forged article to a second forging by changing its mechanical direction (MD) (Patent Document 2).

PRIOR ARTS

Patent Documents

[Patent Document 1] Japanese Patent No. 3215047
[Patent Document 2] Japanese Patent No. 3418350

SUMMARY OF THE INVENTION

Problems to be Solved by the Invention

However, in the forged reinforced articles obtained in Patent Document 1 and Patent Document 2, there are difficult problems to be improved. Accordingly, the problems to be solved by the invention, namely problems of the forged reinforced materials composed of crystalline phase and glass phase at room temperature where a large amount of inorganic fillers are filled are explained by referred PLLA and HA/PLLA composite.

In the molded material which is poly-axially oriented by press-forging the PLLA-only composed of the crystalline phase and glass phase, the poly (lactic acid) exhibits its inherent natures as they are, and since the crystal axes are poly-axially oriented around the MD as a center axis, deferring from uniaxial orientation, the molded material can be reinforced with a little anisotropy of strength. However, when this molded material is used for screws or plates of biodegradable and absorbable bone jointing, it is easy to bend due to its lack of stiffness, and has a fatal defect that the poly (lactic acid) itself has no osteoconductivity.

The present inventor has invented a production method of a molded material where crystal axes are poly-axially oriented as in the aforementioned PLLA by press-forging a HA/PLLA composite prepared by admixing a large amount of bioceramic fine particles to a poly (lactic acid). By filling the inorganic fine particles (bioceramic fine particles), this molded material can be reinforced by remarkable reduction of anisotropy of strength due to anchoring effect at interface of the concavo-convex geometric surface of the fine particles and the PLLA as a matrix, and moreover due to poly-oriented crystals. However since the polymer matrix is diluted due to filling of a large amount of inorganic fine particles with no extensibility, though an apparent stiffness of the composite is improved as a whole, this results in remarkable lowering of softness and flexibility, because the tensile property as a material of the whole composite is decreased proportionally with an amount of the fine particles. An specific shaped final product such as screw is usually produced by preparing a billet of a HA/PLLA composite, preparing a rod by through a forging reinforcement step between Tg and Tm, and then cutting the rod to finish. If there is a direct forging-molding method where the molding process can be achieved at the same time of the forging reinforcement, a yield of material can be extremely improved because any machining waste cannot be generated and the total process are shortened, which results in large reduction of cost. When forging and molding by forcing to push the original billet into a die having an extremely thin portion with pressing, since fluidity is extremely suppressed by the inorganic fine particles, the molding results in entirely failure, or a possibility of success goes down extremely. Therefore, this method can only be applied to a molded material having an extremely simple shape to be selected.

With respect to transfer of the materials when inserting under forging pressure, in the case of PLLA, the material cannot move in a die because the material is in the state of un-processable plastic softening at Tc, and in the case of the HA/PLLA composite, the material cannot move entirely in a whole of die like in the state of processable strain hardening of a metal. The movement in a die becomes so hard when the volume of filler closes to the closest packing, i.e. 33.3 vol % of the whole, it is assumed that the phenomenon in these states is the same as that in the state of processable work hardening of a metallic crystal. Since the interface of the matrix and the inorganic fine particle may be broken when a tensile force is applied outwardly to exfoliate off the interface, a tensile strength of the thus produced molded material becomes remarkably decreased. Namely, extensibility and flexibility are lowered. Of course, this defect can be solved when reducing an amount of the inorganic filler, in other word, when diluting by adding a resin. However, it is nonsense because the properties such as osteoconductivity which are expected along with the amount of filler are lost.

As explained above, each of the PLLA-only to which the bioceramics fine particles are not added and the HA/PLLA composite to which the bioceramics fine particles are added have both physical advantage and disadvantage. Accordingly it has been desired an innovation or invention where the disadvantage of the both are removed and the advantage are maintained and strengthen. However, since the matrix of the both is the same crystalline PLLA, even if the both are simply admixed together, the desired improvement and strengthening cannot be obtained because the advantages are merely diluted to be reduced.

From other point of view, usual methods to blend and mix two or more resins (polymer blending mixing) are classified into the followings.

A) In Case that they are Compatible.
This Case Provides Microscopically Homogeneous Mixing.
  1. Melt mixing
  2. Solution mixing B) In Case that they are not Compatible.
In case of the mixing of A) −1, or −2., there is provided macroscopically homogeneous mixing or macroscopically hetero-componential mixing.

C) Regardless to Compatibility and Incompatibility
This relates to a dry- or wet-blending of granular or abnormal shaped article, provides visually homogeneous mixing which is more macroscopic than those of 1, and 2.

In general, with respect to physical properties, an article made of polymer prepared by microscopically homogeneous mixing gives high strength and has reliability than that prepared by macroscopically homogeneous mixing. Thus in case of compatible materials, there is always employed the A) −1, or −2. mixing methods. A microscopically uniform, homogeneous compatible mixture can be obtained by subjecting to simple solution blend by dissolving the both in a solvent, or by subjecting to melting blend by heating up the both to a melting point or higher to melt and agitating mechanically.

However the resulting mixture has fundamentally their advantages and disadvantages in such a manner as arithmetic average depending on their blending proportion. Therefore, a novel innovation supported by scientific reasons is necessary to enhance physical properties synergistically due to complementary action of each component.

The present invention has been completed under the aforementioned situation, and the objects to be solved are to provide a reinforced composite which has three-dimensional layer-separation structure of a plural of hetero-componential materials having compatible crystalline polymer as a matrix, whereby every inherent physical property of each material is reinforced complementarily, and to provide a method of producing thereof.

Means to Solve the Problems

In order to solve the aforementioned problems, the reinforced composite of the present invention is characterized by comprising a plural of compatible hetero-componential materials having a polymer comprising a crystalline phase and glass phase at ordinary temperatures as a matrix, in which each of the hetero-componential polymer materials forms a micron-sized fibrous layer and the layers are forged in the layer-separation manner that the layers are three-dimensionally crossed and entangled with each other, whereby inherent properties of each material is reinforced complementarily. In other words, the reinforced composite according to the present invention comprises, for example, when including two hetero-componential materials with different kind of properties, the first material comprising a crystalline phase and glass phase at ordinary temperature as a matrix and the second material which is heterogeneous from the first material and comprising a crystalline phase and glass phase at ordinary temperature as a matrix, and, by forging, each of the first material and the second material forms micron-sized fibrous layers which are in the layer-separation manner that the layers are three-dimensionally crossed and entangled with each other.

The forged reinforced composite of the present invention has a crystalline phase where crystalline axes of crystals in the crystalline phase in each layer are not oriented in a certain direction orderly but not oriented uniformly in a given direction but are orientated disorderly in undetermined directions without anisotropy. In other words, according to the forged reinforced composite of the present invention, the crystalline axes of crystals in the crystalline phase in each layer are oriented in the plural directions randomly and disorderly, and thus the composite has a crystalline phase where the axes are oriented randomly and disorderly without anisotropy. A desirable thickness of each layer is from several micron meters to one thousand micron meters. The most practical forged reinforced composite is a composite where the crystalline phase and glass phase at ordinary temperature as a matrix is a crystalline poly (lactic acid), and one layer comprises the crystalline poly (lactic acid) and the other layer comprises a composite of the bioceramics fine particles and the crystalline poly (lactic acid). The one layer and/or the other layer may further contain a non-crystalline poly (lactic acid).

The forged reinforced composite of the present invention can be produced according to the method comprising producing a mixed non-woven fabric in which micro-sized fibers formed of a plural of compatible hetero-componential materials having a polymer comprising a crystalline phase and glass phase at ordinary temperature as a base matrix are three-dimensionally crossed and entangled with each other, producing a dense block by heating under pressure the mixed non-woven fabric at a temperature of a melting point of the polymer or higher to weld in the manner that the relative position of the micro-sized fibers are maintained, and then forging the dense block at a crystallization temperature between a glass transition point and a melting point of the polymer. In other words, the method for producing the forged reinforced composite of the present invention comprises (1) a step of forming micro-sized fibers of a plural of compatible hetero-componential materials having a polymer comprising a crystalline phase and glass phase at ordinary temperature as a base matrix, (2) a step of producing a mixed non-woven fabric in which micro-sized fibers which are three-dimensionally crossed and entangled with each other, (3) a step of producing a dense block by heating under pressure the mixed non-woven fabric at a temperature of a melting point of the polymer or higher to weld in the manner that the relative position of the micro-sized fibers are maintained, (4) a step of forging the dense block at a crystallization temperature between a glass transition point and a melting point of the polymer. The steps (1) and (2) are carried out in the same time.

Explaining the forged reinforced composite of the present invention more specifically, in the forged reinforced composite (molded material) of the present invention, the layer-separated fibrous thin layers to each other of the crystalline polymer or the composite of the crystalline polymer and inorganic fine particles are three-dimensionally crossed and entangled, and, in such a manner that expands all over the molded material, that reinforce the other layer complementarily, which gives a reinforced composite having an enhanced toughness and resistance by the mass of crystals in the layer are oriented in the uncertain directions. The forged reinforced composite of the invention applies effectively to a crystalline polymer comprising a crystalline phase and glass phase at room temperature and having a glass transition point at room temperature or higher, or a composite with inorganic fine particles. For example, it is effective that a composite of a polymer such as nylon, nylon 66, polyethylene terephthalate, polyvinyl chloride or poly (lactic acid) is subjected to hot forging at a proper recrystallizing temperature Tc between a glass transition point Tg and a melting point Tm.

For your information, in case of polyethylene or polypropylene which has a crystalline phase and rubber phase at ordinary temperature, the shape of the forged article such as gears is easily rebounded to the shape before forging due to the rubber phase because of repulsion of the rubber phase by frictional heat, and thus it is not an effective reinforcing method due to crystal orientation. Rubbers with no crystalline phase and polymers composed of glass phase alone are out of the present invention because the shape cannot be fixed and reinforced by crystal orientation.

Specifying to further practical use, from the clinically practical point of view, the present invention is remarkably effective to a composite article implanted in a living body composed of poly(lactic acid) having both of bio-activity and biodegradable and absorbable and an absorbable calcium phosphate (e.g. hydroxyapatite or tricalcium phosphate) fine particles. There can be provided a highly strong medical bone jointing, fixing devices where the properties of the both materials having osteoconductivity are maintained and improved complementarily, because the composite has toughness (good extensibility and flexibility) being inherent to the forged and reinforced poly(lactic acid) and rigidity reinforced by the composite and bio-activity and bio-absorbability.

More specifically, though the forged reinforced composite of the present invention is composed of a plural of compatible polymers as matrix, those polymers are present as continuous layers in the state where the polymers form individual different hetero-componential layers, the layers form fine individual macroscopically homogeneous layers having micron-sized thin thickness (several μm to one thousand μm) over the whole article, and the layers are three-dimensionally crossed and physically entangled without integrated in dissolved or mixed state with each other. The composite of the present invention is based on new concept that, due to forging treatment, the crystalline phase in the layer improves toughness of the materials by finely-divided state and non-orientation of their assembling masses. The organization of the crystal layer assembled creates a specific morphology as if it possibly resembles non-periodic gyroid structure (referring three-dimensional repetitious small curved surfaces which are connected infinitely in cubic directions) in polymer blend system. However, the orientation direction assembling crystalline phase in the micro-sized thin layer is not arranged to a certain direction periodically, but crosses and entangles in the random and non-periodic directions.

Namely, though one of the matrixes is compatible with the other, the blend thereof is in the state of layer separation, and they build up the condition that one layer follows the disadvantageous property of the other layer complementarily, which results in one has a function to follow up the reinforcement with each other.

For example, when applying the present invention to the aforementioned system of PLLA and HA/PLLA, the system includes the same matrix but forms a blended system having the hetero-componential layers, to reinforce with each other the features of trade-off. Namely, even when the matrixes are the same, it is possible that the layer of PLLA and the layer of HA/PLLA are built up to the manner where the layers are three-dimensionally crossed and entangled but are in the layer-separation manner all over the forged reinforced composite (molded material). Thereby, though a total filler percentage of the inorganic fine particles (hydroxyapatite HA) is reduced, the percentage of the inorganic fine particles in the HA/PLLA layer is not changed, and thus the feature due to the filler percentage is not sacrificed. If recovering a filler percentage of the whole molded material reduced by adding the PLLA layer, a filler percentage to the HA/PLLA layer is increased by such a balanced amount.

In conclusion, the PLLA layer contributes to maintain softness, flexibility, tensile strength, elongation, and moldability, and the HA/PLLA layer to maintain hardness, stiffness, scientific and physiological characteristics of the inorganic fine particles adjusted in the filler amount. Therefore, though the matrixes are compatible, the PLLA layer and the HA/PLLA layer can reinforce to each other complementarily in the layer-separation manner. This principal can apply to not only the PLLA system but also any polymers having the phase structure including the crystalline phase and the glass phase at room temperature.

Effects of the Invention

As mentioned above, the forged reinforced composite according to the present invention is composed of a plural of compatible hetero-componential materials having a polymer comprising a crystalline phase and glass phase at ordinary temperature as a matrix. More specifically, in case that a composite is composed of a plural materials such as a composite material containing a thermoplastic polymer having a crystalline phase and glass phase at ordinary temperature which contains inorganic fine particles in a large amount as a functional filler and the same polymer as above alone, or the other compatible polymer therewith, the layer-separated fibrous polymer matrix layers having a thickness of some micron meters to one thousand micron meters forms such a morphological structure that they are three-dimensionally crossed and entangled to spread over the whole composite, and thus the present invention has the following advantages.

(1) To Reinforce Physical Strength and Chemical Features which are Insufficient Properties of One Material by the Other Complementarily The layer of the polymer alone revives the inherent extensibility, softness, flexibility, and the layer of the composite material of the inorganic fine particles and the polymer maintains the inherent hardness, stiffness, high elastic modulus, chemical properties (chemical resistance, etc) physiological properties (bio-activity, bio-absorbability, etc) of the inorganic fine particles, and gives toughness, i.e. toughness to dynamic load to the composite of the present invention.

(2) To Improve Moldability

The layer of the polymer alone has a role to give softness, and the layer of the composite material of the inorganic fine particles and the polymer has a role to give stiffness. Therefore, since the softening deformation ability of the polymer at a crystallization temperature Tc is improved, and moldability in hot forging can be improved, a precise specific complex shaped article can be forged and molded directly by press-forged molding like injection molding. Thus since number of process steps can be reduced and the shaping by machining process can be omitted, a loss of material can be decreased to contribute the reduction of production cost.

(3) To Exhibit the Functions of the Filler (Inorganic Fine Particles) Efficiently Even when the inorganic fine particles are added in a large amount in proportion to the blend ratio of the layer of the polymer alone to the layer of the composite material of the inorganic fine particles and the polymer, the properties do not lose their balance as a whole, and their physical, chemical, physiological properties can be used sufficiently.

BRIEF EXPLANATION OF THE DRAWINGS

FIG. 1 is an explanatory view of the process steps in the method of production of the forged reinforced composite according to one embodiment of the present invention.

EMBODIMENTS TO ACHIEVE THE INVENTION

In the following, one typical embodiment of the forged reinforced composite and method of production of the present invention are explained specifically by referring FIG. 1.

Firstly, the method of production of the forged reinforced composite of the present invention is explained. At first, a mixed non-woven fabric in which micro-sized fibers formed of a plural of compatible hetero-componential materials having a polymer comprising a crystalline phase and glass phase at ordinary temperature as a base matrix are three-dimensionally crossed and entangled with each other (namely, in this embodiment, the aforementioned mixed non-woven fabric is produced almost at the same time as the formation of the micro-sized fibers) is produced. For example, when producing a forged reinforced composite to be used as a highly strong medical fixation and joint devices, a mixed non-woven fabric where the micro-sized fibers of PLLA and the micro-sized fibers of HA/PLLA composite are three-dimensionally crossed and entangled with each other.

The mixed non-woven fabric is produced by dissolving a PLLA in a volatile solvent to prepare a PLLA solution, and mixing HA fine particles with the PLLA solution to prepare a HA/PLLA solution. As shown in FIG. 1(A), a tank 11a of one spray gun 11 is charged with the PLLA solution, a tank 12a of the other spray gun 12 is charged with the HA/PLLA solution. While vibrating and mixing the HA/PLLA solution to prevent the precipitation and separation of the HA fine particles, the PLLA solution and the HA/PLLA solution are ejected vigorously from spray nozzles of the both spray guns 11, 12 to be fibrillated, and sprayed as a mass of fibrous material to a metallic net 13 (net with a surface treating agent to tear off from the net) provided at a distance (around 50 to 100 cm) where the volatile solvent can almost transpire and be dried. At this time, the spray nozzle of each of the spray guns 11, 12 is regulated their positions so that the sprayed PLLA fibers and the sprayed HA/PLLA fibers to the net 13 are not parallel to each other, but are crossed at an angle just before the net 13 or on the net 13 tree-dimensionally and entangled. When this spray is conducted from the front side and the back side of the net 13, a non-woven fabric 14 that the fibers are effectively crossed and entangled three-dimensionally can be obtained. After forming the non-woven fabric 14 having a thickness of around several μm where the micron-sized fine PLLA fibers and the HA/PLLA fibers are crossed and entangled with each other is produced on the net 13, the non-woven fabric is peeled off from the net 13. The mixing ratio of the PLLA fibers and the HA/PLLA fibers can be controlled by selecting a concentration and amount of the PLLA solutions in the tanks 11a, 12a, diameter of the spray nozzle, shape of the nozzle, and the like.

Next, a dense block that micro-fibers of the PLLA and HA/PLLA are melted and fused is produced by heating the mixed non-woven fabric at a melting point of the PLLA or higher under pressure. The dense block can be produced, since the fibers are broken when the non-woven fabric 14 where fine fibers are entangled is agitated, as shown in FIG. 1(B), by avoiding such agitation, charging a given cylindrical die 15 having a bottom with the non-woven fabric, compressing from upper ward with a pressing die 15a under reduced pressure so as to be as dense as possible, heating and melting as it is at a melting point Tm of the PLLA or higher, and then, as shown in FIG. 1(C), cooling down to room temperature. By compressing, heating and melting the non-woven fabric 14 as mentioned above, each of the PLLA fibers and HA/PLLA fibers is melted in its surface, combined together in such a manner as to disappear their fibrous state but remain their position, and thus converted into the dense block 16 (mass body) composed of numerous separated layers (PLLA layer+ HA/PLLA layer). At this time, for easy forging, it is important that a crystalline degree of the dense block 16 is inhibited to be about 30% or less by regulating temperature or period of time.

Alternatively, when charging and compressing a rectangular cylinder die with the non-woven fabric 14, as mentioned hereinafter, it is also possible to press the non-woven fabric 14 from three directions in the order.

Next, the dense block 16 is forged at a proper crystallization temperature Tc between a glass transition point Tg and a melting point Tm of the PLLA. This forging processing may be carried out, for example, in case that a rod-like forging-reinforced composite by using a cylindrical die 17 as shown in FIG. 1 (D1), namely a die 17 having a large diameter cylinder portion 17a and a small diameter cylinder portion 17b and a taper-like diameter-diminishing part 17c where a diameter becomes gradually small, introducing the dense block 16, and pressurizing by the pressing die 17d or the like from upper ward in the inching operation, and then compressing into the small diameter portion 17b.

In case that a plate-like forging-reinforced composite is produced by single forging processing, for example, the composite may be produced by using a die 19 as shown in FIG. 1 (D2), namely, a die 19 where a cylinder portion 19b is provided in the center of the plate-like (disc-like, rectangular, polygon, etc.) molding cavity 19a. Introducing the dense block 16 in the cylinder portion 19b, pressing by using a pressing die 19c from upper ward in the inching operation into the molding cavity 19a. This plate may be a specific shape of article having convex and concave profile, and in this case, the forging is classified to so-called die forging.

In case that a screw of the forging-reinforced composite or the like is produced, for example, the composite may be produced by using a forging molding die 20 as shown in FIG. 1 (D3), namely, a forging molding die 20 where a large diameter cylinder portion 20c is provided, via a tapered cylinder portion 20b, above a small diameter cylinder portion 20a which has a screw groove 20e for forming a screw on the upper inner surface. The dense block 16 is introduced into the large diameter cylinder portion 20c, pressing by using a rotating pressing die 20d from upper ward in the inching operation and rotating bit by bit into the small diameter cylinder portion 20a to form a male thread on the outer surface of the screw groove 20e. This is one of rotational die forging methods.

By forging-processing the dense block 16 according to the aforementioned manner, the crystalline phase and the glass phase of the PLLA in each layer of the dense block 16 are fine oriented crystals containing numerous fine vitreous materials and dispersed homogeneously throughout along with the forging direction, and the mass of the crystalline phase forms, so called, such a layer that the mass does not have a determined orientation direction and is oriented disorderly. The reason why the mass of the crystalline phase does not have a determined orientation direction is that since each of the fine PLLA fibers and HA/PLLA fibers which compose the aforementioned non-woven fabric 14 is three-dimensionally crossed to be intermingled physically in any directions, each of fine fibers faces to any three-dimensional directions in the gyroid, microscopic manner without periodic cycle in a micron-size level, and the trace is remained in the dense block 16 after the melting. Therefore according to the instant embodiment, being different from the conventional method, the mass of the crystalline phase after forging processing is not oriented uniformly and in the determined direction. As mentioned above, the forging-reinforced composite 18 being excellent in toughness without anisotropy in view of strength can be obtained by the dense and homogeneous dispersion of the numerous crystals which are recrystallized more in the forging step and the non-orientation thereof.

Therefore, in the forging-reinforced composite 18 obtained by the aforementioned production method, the hetero-componential materials with compatible polymers having a crystalline phase and glass phase at ordinary temperature as a matrix, namely in this embodiment the PLLA and HA/PLLA are layer-separated with a micron-sized thickness. The every PLLA layer and the each HA/PLLA layer are crossed three-dimensionally and are in the physically entangled manner. Each layer is a layer structure which has a disordered non-periodic gyroid structure where masses of crystal in the crystalline phase which are crystallized by the forging and oriented disorderly without a certain direction in the undetermined directions (in other words, there is a layer structure having a crystalline phase where the crystal axes of the crystals in the crystalline phase are disorderly oriented without a certain direction in the undetermined directions). Since the PLLA layer and the HA/PLLA layer are reinforced complementarily by this layer separation and the masses oriented in the undetermined directions, it is possible to enhance tenacity such as rigidity, ductility, forging ability, extensibility, flexibility or malleability, and toughness such as durability.

In case of a simple polymer composite that inorganic fine particles such as HA are contained in a polymer such as PLLA in an amount of 30 wt % or more, an apparent viscosity becomes remarkably large to lower fluidity at a crystalline temperature Tc between Tg-Tm, and also to make the forging ability lowered. Therefore it is very difficult to produce a fine and precise molded material according to the direct forging molding. This difficulty can be solved by using the layer-separated composite (dense block 16) according to the present invention. Even in case of a small and precise molded material such as mini- or micro-screw having a fine and extremely thin screw part, since the dense block 16 has a proper hardness and flexibility and can introduce into a die directly, as shown in FIG. 1(D3), it is possible to achieve direct forging and molding. Of course, after forming a rod by forging, it is easy to process by machining.

Here, the differences between the forging molding according to the present invention and the usual injection molding in view of thermal properties of resin are explained.

At the time of injection molding, the resin is heated to Tm or higher to melt crystals and is of low viscosity, and has such fluidity as to drop down from a tip of a nozzle by its weight. This molten resin is forced to be injected by an injection pressure into detailed portions of a die, and is introduced under pressure, and thereafter the resin is hardened by cooling of the mold to produce a molded material. An appropriate fluidity of the resin can be selected by regulating the temperature.

On the other hand, the forging molding is a method where a resin is forged from the aftermost of a billet into a die while moving in the inching operation at a crystalline temperature Tc between Tg-Tm where the resin does not have a fluidity where the resin drops down by its weight, and is deformed into a molded material, and then is hardened by cooling. In case that a billet is composed of constant and homogeneous composition as the whole, during the forging, the crystals are oriented along in a certain direction by abrasive stress along with the inside surface of the mold, the reinforcing effect can be exhibited by increasing a crystallinity due to advance of recrystallization. For example, this case is the case that the billet is made of the PLLA-only, or the case of the HA/PLLA composite.

The billet (dense block 16) of a pre-molding stage prepared according to the method of the present invention forms layers having different natures even though they are compatible with each other, and has a structure of micro-sized layers which have traces of the fibers and are three-dimensionally intermingled without no determined direction. Therefore, when the forging is carried out by inserting under pressure into the small diameter cylinder portion 17b of the die 17 having the taper-like diameter-diminishing part 17c in the middle position as shown in FIG. 1(D1), the fine particles of gathered chain of the crystalline phase which contains glass phases oriented in every direction within the layer and subjected to stress along with the tapered angle α of the taper-like diameter-diminishing part 17c are recrystallized by the pressure of movement in the inching operation from above, an thus mass of crystalline phases with no direction are dispersed homogeneously all over the system. As the result, the forging-reinforced composite 18 having no anisotropy of strength can be obtained. However, for moving a material through the die during the forging molding, the material must have both properties of processing hardness observed in metal and pressured softening observed in plastics. In the dense block 18 in the present invention, two separate layers intermingled with each other complementarily, the material can penetrate into a special die having specific and relatively complex shape with thin part, as shown in FIG. 1(D1), a screw and other article having an abnormal shape can be forged directly.

Next, by referring a forging-reinforced F-HA/PLLA composite which is suitable to a bone jointing for surgical use which requires high strength and toughness, possibility of the direct forging molding is explained.

Since a forging-reinforced F-HA/PLLA composite containing HA fine particles in a large amount of 30 to 40 wt % has an extremely lowered thermo-fluidity than the case of PLLA-only at the forging temperature, it is difficult to forge and mold directly a fine, precise molded material such as mini- or micro-screw. Especially, a devise having a relatively long length of 10 mm or more cannot almost be forged and molded directly.

On the other hand, in case of PLLA-only, since it can be so softened at a crystalline temperature Tc of 100° C. or higher between Tm-Tg, it is possible to forge and mold directly a simple article such as a rod by press-forging process steps. However, it is difficult to forge and mold directly the aforementioned fine, precise, relatively long and complex molded material such as mini- or micro-screw. The reasons are as follows.

In order that a resin moves through a narrow pathway for the thin part of article by intermittent pressure force during the forging, it is required a high viscosity of such an extent. Namely, when a rod (billet) before forging is introduced into a complex die having a specific shape under forging pressure, the resin firstly introduced into the die moves in the die by the pressure for movement in the inching down behavior from the aftermost of the rod. At that time, the PLLA must have a high viscosity enough to transmit the pressure from the aftermost to the top of the rod. However, the PLLA does not have such a hardness and high viscosity, and exhibits the thixotropic softening phenomenon due to receiving pressure load at a glass transition temperature or higher which is inherent property of plastic materials. Therefore, the resin does not have faculty to transfer the pressure to move in the die by pushing force, the PLLA rod cannot move anymore in the die, which results in failure of filling. Thus it is impossible to forge directly such a specific complex article having a thin part.

Namely, since the material HA/PLLA and the material PLLA have trade-off properties. It is very difficult to forge and mold directly a relatively long article having a complicate specific shape and a thin part. However, according to the reinforced composite of the present invention having the layer separation morphologic construction, it can be solved. And the both properties of hardness and softness are balanced, and thus the resistances to dynamic and repetitive load such as tenacity and toughness. As a result, it is improved and can prevent a screw or plate made of the forging-reinforced composite of the present invention from breakage at the insertion to a body or just thereafter. In case of the plate, since ductility, forging ability, extendibility, malleability, and the like are improved and, in addition, the anisotropy of strength is also solved, by considering strength after forging reinforced, it may not be necessary to select cutting directions of Mechanical Direction MD, the Transversal Direction TD thereto, the Diagonal Direction DD. Since reliability of the bending deformation at ordinary temperature is remarkably increased and easy, the bending deformation procedure during operation can be done reliably without heating. Further, when adding an amorphous PDLLA (poly-D/L-lactic acid copolymer) which is compatible with the crystalline PLLA, since biodegradation in a body is accelerated, there is an advantage that absorption and disappearance rates after the operation are enhanced, and remaining of unnecessary foreign materials in a body for a long time can be avoided.

Next, it is more specifically explained the reason why the anisotropy of strength by crystal orientation can be solved.

According to the reinforcing method by uniaxial drawing, since the crystals orientation align in the uniaxially drawn direction, the strength in the mechanical direction MD of the drawn direction can be increased, but the strength in the transversal direction TD to MD cannot be reinforced. Therefore, considerable anisotropy of strength due to the difference of strengths between MD and TD, which results in many occurrence of longitudinal crack along with MD even if MD is reinforced. According to the press-forging method (the aforementioned Patent Document 1) which has been previously invented by the present inventor where the material is forced to be introduced under pressure from the large diameter cylinder portion to the small diameter cylinder portion through the taper-like diameter-diminishing part, since the crystals orient in the direction of numerous inclined axes which direct from outer peripheral to center axis inwardly with an inclined angle similar to the tapered angle of the taper-like diameter-diminishing part, the extreme anisotropy of strength shown in the uniaxial drawing has disappeared. However, even if an optimum inclined orientation of crystals is selected by changing the tapered angle of the taper-like diameter-diminishing part, in other words, even if an optimum crystal orientation ratio, i.e. r value (Diameter $R_1$ of the large diameter cylinder portion/Diameter $R_2$ of the small diameter cylinder portion) of orientation ratio is selected, the anisotropy of strength cannot be solved and yet remains in quite a lot.

In the method of aforementioned Patent Document 2 where the plate or rod produced by the first pressurized forging method is cut, and subjected to the second press-forging method in the direction transversal by 90 degrees to the mechanical direction MD, since the second orientation directs in the TD direction with respect to the first MD, the anisotropy of strength can be solved remarkable. However, because the anisotropy due to the first anisotropy still remains, the anisotropy of strength does not disappear completely. As shown in the data of toughness of repeated bending of the reinforced molded material made by the twice forging method in the MD, TD, DD disclosed in the literature [Biomaterials 22 (2001)3197-3211], the anisotropy remains considerably.

To the contrary, according to the present invention, almost of the anisotropy can disappear by the first press-forging, and by the second forging the anisotropy can disappear to a complete extent. The reason is explained in the following.

As shown in FIG. 1(A), a PLLA solution in dichloromethane is sprayed from one spray gun 11, and a HA/PLLA solution prepared by adding HA fine particles to a PLLA solution is sprayed from the other spray gun 12. By this spraying, remarkably fine fibers of several µm to several dozen µm level where a solvent is almost volatilized are gathered to form PLLA fiber bundle (yarn) and HA/PLLA fiber bundle (yarn) of several dozen µm to several hundred µm. These bundles are crossed and entangled to produce a non-woven fabric 14 where the both are in disorderly mixed state. The crystallinity of the PLLA fiber and the HA/PLLA fiber which are sprayed from spray nozzles of the both spray guns 11, 12 and fibrillated at lower than Tc is assumed that the crystals orient in the direction of the longitudinal axis of the fiber (yarn) as is similar to the uniaxial drawing, because the crystals are fibrillated by spraying force while evaporating the solvent at room temperature which is lower than the boiling point (39.75° C.) of the solvent (dichloromethane). However, it is not so high in case that uniaxial drawing is carried out by cooling to the crystallizing temperature after melting.

Next, as shown in FIG. 1(B), this non-woven fabric 14 is packed into the die 15 so as to introduce to every corner and part of the die while avoiding from cutting the fibers. After that, by compressing as dense as possible so that there is no space between the fibers under reduced pressure at room temperature, a dense body can be formed while maintaining substantially the relative position of the fibers before packing. At this time, if the compression is carried out not only from upper ward but also from side, the relative position of each fiber in the non-woven fabric 14 can be basically maintained without shifting. For example, by compressing a regular cube from upper side to a certain height firstly, standing the compressed article vertically, inserting into a die having the same cavity as profile of the compressed article, compressing from upper side again, and then compressing the remaining surfaces of the compressed article in the same manner, a compressed article which is compressed form three directions and maintains the relative position of the fibers before compression can be produced.

By heating the dense non-woven fabric 14 to a temperature of the melting point Tm or the PLLA or higher as it is, the PLLA fibers and the HA/PLLA fibers are melted on their inter surfaces to be integrated, and the PLLA and the HA/PLLA are separated as layers in the manner that traces of the positions of the fibers are remained while maintaining their positions to form a dense block 16 without cavity. At this time, in order to carry out easily the next pressured forging shown in FIG. 1 (D1), (D2), (D3), it is preferable to control the degree of crystallization to about 30% at most or less by regulating temperature and period of time. In the die 15, mixing procedure by a screw, etc. should not be done, and the fusion should be carried out by standing with compression. Thereby, the relative positions of the PLLA fibers and the HA/PLLA fibers are maintained as they are, and melted, cooled and fixed. When heating, the PLLA matrixes of the both fibers are fused at the inter surface to be integrated. Since the inorganic fine particles HA exist only in the HA/PLLA fiber, there forms a structure where the particles are microscopically maldistributed only in the state of dispersing along with the trace of the HA/PLLA fiber in the non-woven fabric 14 of mixture of the both fibers. Namely, in the dense block 16 of FIG. 1(C) before forging, the inorganic fine particles HA are not homogeneously dispersed all over the PLLA of the fused block, but are maldistributed and dotted at the position of the HA/PLLA fiber. One of the main subject matters of the present invention is to produce the structure.

Next, as a result of carrying out the forging step by selecting a crystallizing temperature Tc between Tg-Tm as shown in FIG. 1(D1), (D2), (D3), the crystalline phase and the glass phase in the PLLA of each layer in the dense block 16 form numerous fine crystal particles containing vitreous substance which are dispersed all over homogeneously. Since the crystal particles form a layer structure where the masses of the crystalline phase do not orient in the determined direction, the anisotropy can almost disappear by one forging processing step.

Examples of forging method for metal include, as explained after, cold forging, hot forging, heat forging, press forging, free forging, precise forging, die forging, ring forging, rolling forging, and the like, are selected by matching with shapes, reinforcements, uses. In the present invention, a forging method may be employed by selecting from those forging methods considering the desired products. Accordingly, the layer structure of disordered orientation of the crystalline phase may be different.

Next, in forging of a metal, crystal fine particles are finely divided uniformly, which results in improvement of strength. With respect to a plate of the composite of the present invention, the crystals are finely divided by repeated press-forging by using a servo press. Accordingly, the reinforcement of properties by fine dividing of plastic crystals and disordered orientation of crystals is explained in comparison with the case of metal.

Generally, metal has a property that resistance to deformation becomes large when a crystal becomes small. This is so called as Hall-Petch's Law. The plastic deformation indicates that a deformed shape cannot return to the initial shape even after removing the applied force. This is so called as permanent strain (permanent deformation). When a metal is plastically deformed, the deformed metal is harder and stronger than the initial state. This is so called as work hardening. The main reason of the plastic deformation is due to movement of dislocation of crystal, and there are various processing methods for reinforcing metal by utilizing the work hardening caused during the plastic deformation. Elastic deformation is a deformation that, in Stress-Strain Curve, a deformed shape of the metal can return to the initial shape from the starting point to the final point E of the linear portion according to Hooke's Law, when removing completely the applied load. This is so called as elastic deformation. When beyond the point E, the plastic deformation governs its deformation, until a breakdown point, even removing the load, the deformed shape does not return to the original shape and the permanent strain remains. Deformation and molding may be done by utilizing this property. With respect to metal, after the plastic deformation, the work hardening occurs.

Though plastics also deform according to the stress-strain curve, even if the deformation is elastic deformation within the range of elastic deformation until the point E, it is always that the deformed shape cannot return to the initial shape perfectly due to elastic relaxation of the rubber phase and glass phase. At this time, the deformation returns to an analogous original shape remaining hysteresis loss in hysteresis loss curve therein. This property is not same as the hysteresis curve of metal. Anywhere, apart from chemical treatments such as intermolecular crosslinking which changes physical properties, it is necessary to attempt to reinforce physical properties by physical (mechanical) treatment to provide the micro-crystallization or specific crystal orientation.

In case of metal, there have been studied various working methods in order to reinforce by finely dividing through recrystallization. Among them, the forging is an extremely useful method where physical properties are reinforced by fine-dividing and orientation of crystals. This is a working method where a pressure is applied to a material via a tool to finely divide crystal particle and make crystalline structure uniform, and then the material is formed to a desired shape. By the forging the toughness of a material becomes increased. The press or die forging is a method where a desired product is produced by packing and compressing a material into a flat mold or a mold having the profile of the product. Others are free forging, die forging and rotational forging. The cold forging carrying out at room temperature is employed for producing various functional parts and many parts such as gears, bolts, and nuts. After forging, properties of material such as strength can be improved due to work hardening. On the other hand, the worm (hot) forging is a processing method where a material is heated to a recrystallization temperature or higher to reduce its resistance to deformation due to enhancing its ductility. Since recrystallization causes after processing, the work hardening does not happen, but the properties of material can be improved by fine-dividing of structure and disappearance of voids.

On the other hand, with different morphology from metal, some plastics have crystalline phase as molecular assembly. However, among plastics composed of molecular assembly arranged by long chain polymers in which monomers are linked together, solid plastics at ordinary temperature may be classified, from viewpoints of difference of intermolecular force due to structural chemical bonding style, a rubber phase (amorphous), glass phase (amorphous and medium nature between rubber phase and crystalline phase), and crystalline phase (crystalline). Practically, a plastic of 100% crystalline phase does not exist. Methods for reinforcing the plastics having these phases are chemically reinforcing methods for forming a three-dimensional network by crosslinking or vulcanization. However, an article prepared by three-dimensional network may return its shape after plastic deformation, and thus the plastically deformed shape cannot be fixed. Kinds of the phases formed at room temperature are classified to the rubber phase alone, the glass phase alone, combination of the rubber phase and crystalline phase, and combination of the glass phase and crystalline phase. Among them, it is said that the polymer composed of the crystalline phase and glass phase at room temperature is a phase structure which shows most analogous behavior to metallic crystal in view of phase structure. Accordingly, when forging the polymer having such a phase structure, it is assumed that a composite molding article having reinforced and improved toughness can be obtained due to crystal minimization and crystal orientation. The present invention has been made according to this concept.

When the dense block 16 moves by the press-forging as the compressive forging in the cylindrical die 17 having the large diameter cylinder portion 17a and the small diameter cylinder portion 17b and the taper-like diameter-diminishing part 17c, as shown in FIG. 1 (D1), the crystals in the crystalline phase of the PLLA are rearranged and orientated along with the taper-like diameter-diminishing part 17c while crystallizing by recrystallization. However, the degree and structure of orientation may be different depending upon the deformation ratio (orientation ratio) γ value (Diameter $R_1$ of the large diameter cylinder portion/Diameter $R_2$ of the small diameter cylinder portion). To the dense block 16 are applied stress having many axes from outer ward to the inside center axis at a taper angle of α degree to the MD. The part where the HA fine particles are present moves in response to the stress from the taper-like diameter-diminishing part 17c. The HA/PLLA fibers, however, cannot move by sifting largely to the layer of the molten PLLA-only where the PLLA fibers are melted from the molten HA/PLLA layer. The reasons are that the PLLA does not have fluidity so as to deform by its weight at a crystallization temperature Tc, and that any forced mixing is not applied.

At this time, the crystallinity in the PLLA layer and the HA/PLLA layer are different, and the manners of those are explained herein below.

In general, the PLLA is a polymer having a relatively low crystallization speed, and to speed up, there are reported various poly (lactic acid) resin compositions in order to improve the crystallization rate by the effect of a nuclear forming agent. Examples are a composition of poly (lactic acid) and a lamellar clay mineral, a composition of poly (lactic acid) and a crystalline $SiO_2$, a composition of poly (lactic acid) and an inorganic particle such as talc boron nitride, a composition of poly (lactic acid) and a nuclear forming agent such as talc, a composition of poly (lactic acid) and a lamellar silicate, and a like.

From the present inventor's experiences, addition of a large amount of the HA fine particles contributes the acceleration of crystallization. When crystallinity at a crystallization temperature Tc is about 50% or more, since it is difficult to soften due to progress of further hardening, it is well known that forging molding is impossible. Therefore a large amount of the HA fine particles is filled up, and the crystal structure of the PLLA matrix in the site layer yielded by melting the HA/PLLA fibers is different from that of the layer of PLLA alone yielded by melting the PLLA fibers, that is, the structure of the fine crystalline particles is different even under the same thermal history to be applied, and crystallinity is seemed to be relatively high. Namely, in view of the crystal structure and the crystallinity, it is said that they form separated layers having different properties.

Here, there is further explained the change of structure of crystal orientation and contribution to strength after press-forging.

When carried out press-forging and molding the HA/PLLA which is a homogeneously dispersing composite system all over a molded material, the crystal orientation can be achieved all over the material under the same condition. However, when press-forging and molding the material (dense block 16) of the present invention which has the layer separation structure where the PLLA and HA/PLLA are disorderly dispersed, the crystal phases in the disordered separated layer orient without order. As shown in FIG. 1(D1), even when forging is carried out by orienting the crystals with multi-axial directions through the taper-like diameter-diminishing part 17c having a degree, the PLLA near the HA fine particle which is present in the trace of the molten HA/PLLA fiber and acts as a nuclear forming agent is growing as a crystal to increase its crystallinity, and then the crystal orientation along with the taper-like diameter-diminishing part 17c has been completed. As to the direction, the position of the disordered fine particles in the dense block 16 is taken over. During the forging, though each fiber layer is deformed, the crystals are arranged in the manner of rearrangement in the fiber layer which is strained by the deformation.

One of the reasons why a cold forging at room temperature or lower cannot be employed for PLLA is that there is a case where, since the room temperature is lower than the body temperature, a device prepared by the cold forging may restore its original shape i.e. before the forging, for example, when embedding in a human body as an implant, and such a device may not be useful for clinical uses. Since the glass transition temperature Tg is about 65° C., when selecting a proper crystallization temperature Tc between Tg that is higher than a body temperature to the melting point Tm, and carrying out the hot forging at that temperature, improvement of strength can be established because obtaining the recrystallization, the crystal minimization and the crystal orientation. In case of a flat device such as a plate used as a bone jointing, by carrying out the press-forging by a servo-press on the upper and lower surfaces repeatedly, the crystalline fine particles can be accomplished, and thus, toughness to dynamic load such as repeated bending is considerably improved. In the present invention, since a plural of the hetero-componential fiber layers having a layer thickness of from a micron (1 μm) to micro-meso (100 to 1000 μm) are repeatedly subjected to press-forging in all directions in the three-dimensionally crossed and intermingled manner, the crystals in the crystalline fine particles do not orient in the determined direction but orient in every direction. Thus the anisotropy of strength in every axial direction of X, Y and Z can disappear. The intermingled structure of the fiber layers, structure of crystal orientation and anisotropy etc. can be controlled by selection of spraying method (crossing angle, same spray, alternate and intermittent spray, spray from both front side and back side, shape of nozzle orifice, number of nozzles, etc) at the spray step shown in FIG. 1, and a preferred method may be selected optionally. By providing a plural of nozzle orifice which spray the aforementioned hetero-componential materials in front of one nozzle, and spraying, those materials are intermingled on the targeted net. In this case, according to the method for packing the non-woven fabric at the packing in the die shown in FIG. 1(B), more three-dimensionally intermingled structure can be obtained.

According to the present invention, the crystal orientation is different from that prepared by forging of uniform system of the HA/PLLA, and the HA fine particles are microscopically maldistributed in the HA/PLLA layer, the crystals form such a structure that, having different crystal size and crystallinity in the layer of PLLA-only and the HA/PLLA layer, the crystals are dispersed all over the molded material with disordered manner. This contributes the properties. Namely, the layer of PLLA-only derived from the molten PLLA fibers has a lower crystallinity than that of the HA/PLLA to maintain its flexibility, and compensates effectively the poor flexibility of the HA/PLLA crystalline layer derived from the molten HA/PLLA fibers in a relatively high proportion. The latter layer maintains properties such as hardness and stiffness as the forging-reinforced composite. If desiring the same functionality such as bio-activity as that of the homogeneous HA/PLLA forging-reinforced composite, a proportion of the HA fine particle in the HA/PLLA layer is increased by such an amount that the proportion diluted by adding the PLLA layer is compensated to balance in the whole. In this case, the both layers act complimentarily to reinforce and maintain effectively the various properties such as durability of materials, toughness, tenacity, ductility, forging ability, extendibility, and malleability. For example, as shown in the forging-reinforced composites 1 to 4 in Examples mentioned after, even if a proportion of the layer of PLLA-only is low as approximately 5 to 10 wt %, since the layer is fibrous and dispersed all over the molded material, it exhibits its effect sufficiently in the direct forging and molding of a molded material.

In the above, in order to explain the forging-reinforced composite which is suitably used to surgical medical tool such as a fixation and joint devices, a bio-degradable and absorbable crystalline poly(lactic acid) is used as the matrix polymer composed of the crystalline phase and glass phase at normal temperature, and there is selected that one layer is a crystalline poly(lactic acid) and the other layer is a composite of a bio-ceramic fine particles such as a bio-absorbable un-sintered or un-calcined HA and the crystalline poly(lactic acid), but the present invention is not limited to this embodiment. The present invention can be applied widely to crystalline polymers composed basically of a crystalline phase and glass phase at room temperature and having a glass transition temperature of room temperature or higher such as Nylon, Nylon 66, polyethylene terephthalate and polyvinyl chloride, and a composite with an inorganic fine particle. Moreover, the bio-ceramic fine particle is not limited to the HA, and examples of the fine particle include uncalcined or unsintered dicalcium phosphate, tricalcium phosphate, tetracalcium phosphate, octacalcium phosphate, calcite, seravital, diopside, natural coral and the like.

In the following, the present invention is explained specifically by referring Examples.

Example 1

Dissolution of PLLA and Preparation of Dispersion of Inorganic Fine Particles (A) Case of producing, by one forging, a rod for bone fixation device such as bone-fixing screw, pin or nail, as a forging-reinforced composite, which is a rod to produce a final product by machining, or case of producing a final product by direct forging molding by one step;

An about 3% PLLA solution was prepared by dissolving a poly (lactic acid) having a viscosity average molecular weight (Mv) of about 300,000 in dichloromethane. On the other hand. HA/PLLA dispersions were prepared by dissolving a poly(lactic acid) having a Mv of about 300,000 in dichloromethane and adding and dispersing unsintered and uncalcined absorbable HA fine particles having an average particle size of 3 to 5 μm, in the following manner.

Namely, when producing forging-reinforced composites of Sample numbers 1, 3, 5, 7, 9 in the following Table 1 where content of the HA fine particles was about 30 wt %, considering a ratio (mass ratio) of PLLA and HA/PLLA, contents of the HA fine particle in the HA/PLLA were regulated to 31.5 wt %, 33.0 wt %, 34.5 wt %, 36.0 wt %, 39.0 wt % to prepare HA/PLLA dispersions having the PLLA component of 3 to 5 wt %.

As shown in Sample numbers 2, 4, 6, 8, 10 of Table 1, when producing forging-reinforced composites where a content of the HA fine particle in the HA/PLLA was constant at 30 wt %, a HA/PLLA dispersion having the PLLA component of 3 to 5 wt % and having the content of the HA fine particle in the HA/PLLA of 30 wt % was prepared. In the forging-reinforced composites of Sample Nos. 2, 4, 6, 8, 10, though a content of the HA fine particle in the composite was decreased with the increase of the proportion of the other PLLA layer, since the HA/PLLA layer was dispersed all over the composite, the bio-activities such as osteoconductivity and bio-absorbability were not changed essentially.

TABLE 1

Composition of layer-separated forging-reinforced composite

| Sample No. | One layer | Other layer | PLLA:HA/PLLA (Mass ratio) | HA content in reinforced composite (wt %) |
|---|---|---|---|---|
| 1 | PLLA | HA/PLLA (HA: 31.5 wt %) | 5:100 | 30 |
| 2 | PLLA | HA/PLLA (HA: 30 wt %) | 5:105 | 28.6 |
| 3 | PLLA | HA/PLLA (HA: 33.0 wt %) | 10:100 | 30 |
| 4 | PLLA | HA/PLLA (HA: 30 wt %) | 10:110 | 27.2 |
| 5 | PLLA | HA/PLLA (HA: 34.5 wt %) | 15:100 | 30 |
| 6 | PLLA | HA/PLLA (HA: 30 wt %) | 15:115 | 26.0 |
| 7 | PLLA | HA/PLLA (HA: 36.0 wt %) | 20:100 | 30 |
| 8 | PLLA | HA/PLLA (HA: 30 wt %) | 20:120 | 25.0 |
| 9 | PLLA | HA/PLLA (HA: 39.0 wt %) | 30:130 | 30 |
| 10 | PLLA | HA/PLLA (HA: 30 wt %) | 30:130 | 23.0 |

(B) Case of producing a plate for bone fixing as a forging-reinforced composite by twice forging steps:

In case of plates, since bio-activity to directly contact and bonding to bone effectively is importantly considered, it is desired to blend the HA fine particle in a large amount, and a 40 wt % content is now used for clinical use. These are reinforced by twice forging procedures for avoiding the anisotropy of strength, i.e. second forging being carried out by changing the forging direction by 90 degree, namely changing the direction from MD to TD.

An about 3% PLLA solution was prepared in the same manner as in the (A). On the other hand, when producing forging-reinforced composites of Sample Nos. 11, 13, 15, 17, 19 in the following Table 2, contents of the HA fine particle in the HA/PLLA were regulated to 42.0 wt %, 44.0 wt %, 46.0 wt %, 48.0 wt %, 52.0 wt % to prepare HA/PLLA dispersions having the PLLA component of 3 to 5 wt %. When producing forging-reinforced composites of Sample Nos. 12, 14, 16, 18, 20 of Table 2, a HA/PLLA dispersion having the PLLA component of 3 to 5 wt % and having the content of the HA fine particle in the HA/PLLA of 40 wt % was prepared.

TABLE 2

Composition of layer-separated forging-reinforced

| Sample No. | One layer | Other layer | PLLA:HA/PLLA (Mass ratio) | HA content in reinforced composite (wt %) |
|---|---|---|---|---|
| 11 | PLLA | HA/PLLA (HA: 42.0 wt %) | 5:100 | 40 |
| 12 | PLLA | HA/PLLA (HA: 40.0 wt %) | 5:105 | 38.1 |
| 13 | PLLA | HA/PLLA (HA: 44.0 wt %) | 10:100 | 40 |
| 14 | PLLA | HA/PLLA (HA: 40.0 wt %) | 10:110 | 36.3 |
| 15 | PLLA | HA/PLLA (HA: 46.0 wt %) | 15:100 | 40 |
| 16 | PLLA | HA/PLLA (HA: 40.0 wt %) | 15:115 | 34.7 |
| 17 | PLLA | HA PLLA (HA: 48.0 wt %) | 20:100 | 40 |
| 18 | PLLA | HA/PLLA (HA: 40.0 wt %) | 20:120 | 33.3 |
| 19 | PLLA | HA/PLLA (HA: 52.0 wt %) | 30:130 | 40 |
| 20 | PLLA | HA/PLLA (HA: 40.0 wt %) | 30:130 | 30.7 |

(Concrete Explanation of Production Steps)

Tanks 11a and 12a of double spray guns 11 and 12 shown in FIG. 1(A) were charged with the PLLA solution and the HA/PLLA dispersion, respectively. Selecting proper spray nozzles, they were forced to be sprayed from the nozzle openings in regulated amounts to be sprayed by pressurizing with compressed air while shaking the dispersion so as not to precipitate the HA fine particles to a net 13. The net was made of metal with surface treating agent and the mesh with a proper open area, and was set at a distance of about 50 to 100 cm. The sprayed materials are adhered on the net 13 in the manner of hanging the very fine fibers which were dried after evaporating the solvent, by blowing out and crossing, by spraying the PLLA solution and the HA/PLLA dispersion alternatively, or by spraying from front side and back side. In this case, since the HA/PLLA dispersion which was prepared by mixing the HA fine particles and the PLLA solution was solidified in the fine fibrous material before precipitating and separating unevenly, fine fibers dispersed homogeneously could be prepared even when a concentration of the HA fine particles was high. Further, according to this method, since aggregating mass which are easily yielded by secondary aggregating when the HA fine particles were added gradually to the solvent with stirring could be avoided, the HA/PLLA fibers where the HA fine particles were dispersed very homogeneously could be obtained. Since it has been confirmed that the present method was one of useful methods that a composite where the HA fine particles having a high concentration of 50 to 85% were dispersed uniformly, it is possible to control to prepare every concentration by regulating an amount of the PLLA to be added to a very highly concentrated HA/PLLA fiber. Fibers of approximately 1 to 10 μm diameter were sprayed from each nozzle opening, the sprayed fibers were hung on the target net 13 to gather as fiber (yarn) bundles of 30 to 100 μm, which could form a non-woven fabric 14 where the PLLA fibers and the HA/PLLA fibers were three-dimensionally crossed and entangled. When a thickness of the fibers was built up to several mm, the non-woven fabric 14 was peeled off from the net 13. This working was conducted in a closed room where an apparatus which could suck and perfectly recover the solvent was installed. The recovered solvent was repeatedly recycled many times.

(Ratio of PLLA Fibers and HA/PLLA Fibers)

Considering the bio-activity such as osteoconductivity and mechanical strength of the usually clinically usable HA/PLLA devices (HA content of screw and pin, etc being 30 wt %, HA content of plate, etc. being 40 wt %), the mass ratio of the PLLA fibers (layer) to be admixed to the HA/PLLA fibers (layer) is suitably 5 to 40 parts by mass as shown in Table 1 and Table 2, preferably selected in 10 to 20 wt %. In this case, there are a method where the total amount of the un-sintered and un-calcined HA fine particles is 30 wt % or 40 wt % (cases of Sample Nos. 1, 3, 5, 7, 9, 11, 13, 15, 17, 19), and a method where only the HA/PLLA fibers (layer) is 30 wt % or 40 wt % (cases of Sample Nos. 2, 4, 6, 8, 10, 12, 14, 16, 18, 20). Even in the latter case, since the HA/PLLA layer spreads continuously to every part of the molded material in the entangled and layer-separation state with the PLLA layer, through this layer having a very high HA content, the bio-active function can be exhibited on the both surfaces of the molded material as is seen in a device composed of only the HA/PLLA composite of 30 wt % or 40 wt %. Accordingly there is no practical difference in the present bio-activity and bio-degradation behavior, and moreover sufficient effects can be obtained, because the physical properties of the PLLA layer compensates the disadvantages of the HA/PLLA device.

Next, the non-woven fabric 14 was packed into a cylindrical die 15 with a base in the manner that it reached every part continuously without cutting, or in the manner that it was cut to a length applicable to the die size. Then, while de-aerating under reduced pressure, by compressing under pressure from the upper with a columnar pressing die 15a having the same outer diameter as the inner diameter of the die 15, a dense rod-like compressed mass was produced. In case of a square cylinder die, by deforming from the upper surface and the both side surfaces stepwise, and then packing in a die having the same cavity and pressurizing to produce a cubic block, the initial relative relation of the entangled state of the very fine fibers can be surely kept effectively.

After that, while maintaining the compressed condition, the die 15 was heated to 185 to 190° C. which was little higher than the melting point Tm of the PLLA under vacuuming. At this time, since the PLLA was melted and each of the PLLA-only fibers and the HA/PLLA fibers composed of the non-woven fabric 14 were fused to be integrated at the interface thereof under de-aeration and reduced pressure while vacuuming, the fiber bundle of 30 to 100 μm was converted to a thinner molten body, and then a rod-like dense block 16 could be obtained. It has been confirmed by a simple X ray or micro CT that the PLLA and HA/PLLA in the dense block 16 were separated in the form of layer while remaining the trace of maintaining the relative positions of the fibers at the packing to the die. By adding a pigment to one of the PLLA solution or the HA/PLLA dispersion to be colored, the layer separation could be observed with an optical microscope. Namely, there could be produced a rod-like dense resin block having a structure where the PLLA layer and the HA/PLLA layer are three-dimensionally entangled with each other in the form of net-work. At this time, the viscosity average molecular weight Mv of the PLLA was lowered to about 200,000 to 250,000 due to the thermal history.

Next, this dense block was inlet to the large diameter cylindrical part 17a of the die 17 for forging as shown in FIG. 1(D1). The die 17 is a standard die having the taper-like diameter-diminishing part 17c between the large diameter cylinder portion 17a at the upper side and the small diameter cylinder portion 17b at the lower side. The deformation ratio of forging, i.e. r value (Inner diameter $R_1$ of the large diameter cylinder portion/Inner diameter $R_2$ of the small diameter cylinder portion) is selected with in the range of 1.3 to 3.5 where movement and deformation of the material can be technically possible by the press-forging, and by the value the strength of the obtained reinforced composite 18 may vary within a certain range. The taper angle α of the diameter-diminishing part 17c is an important factor to determine the value r, and it is preferable to select 30 degrees or less in order to make movement of the resin easy.

The dense block inserted to the large diameter cylindrical part 17a of the die 17 was subjected to the press-forging by compressing from the upper side by moving a metal pressing die 17d in the inching operation. The temperature at this time was a crystallizing temperature Tc of the used PLLA which was the melting point T or lower and the glass transition temperature Tg or higher. Considering a degree of crystallization of the PLLA, within the range of 95 to 110° C., a proper temperature which complies with the HA blending ratio, ratios of mass or volume of the PLLA and HA/PLLA may be selected. In this Example, the deformation ratio, i.e. r value and the crystallizing temperature Tc were 2.8 and 103° C. respectively, being similar to those of Document [Biomaterial 20 (1999)859-877]. According to the layer-separated composite of the present invention, however, since the movement of the resin in the mold was improved at Tc, an experiment at a high deformation ratio, i.e. r value of 3.2 was carried out.

Example 2

According to the method of the present invention, due to the specific structure formed by the layer separation of two components, the anisotropy of strength can be improved even by one servo press forging. Here the present inventor has studied a method where the anisotropy of strength could be improved more surely by one servo press forging when producing a flat plate. When producing the flat plate, since the crystal orientation may be generated in the direction of the applied pressure in the one compression forging, a residual strain may be remained due to material movement. Namely, it is afraid that there may be a difference of strengths between the longitudinal direction and the transverse direction of the rectangular plate or a plate in which a rod is cut out. In order to reinforce and improve the anisotropy of the crystal arrangement more surely by solving the residual strain and micro-crystallization, it has been confirmed that when carrying out the so-called second forging by changing TD and MD, the anisotropy of strength could be solved. Though the deformation ratio. i.e. r value range of this case was usually 1.5 to 3.0, the forgings were carried out at 2.3 both in the first forging and the second forging. From the plate, a plate of the same form as a mini plate of titanium which has been well used in the present oral, maxillofacial surgery was produced by punching, and fundamental properties thereof were measured. The toughness to the repeated bending of the mini plate punched out from the flat plate is shown in Example 5 mentioned after.

Example 3

In this Example, a possibility to direct forging and molding of a precise molded material was investigated. The same PLLA and HA fine particles used in Example 1 were used. A die for forging which was very similar to a mini screw of Leibinger type for dental surgery of under Jaw was fabricated. A top diameter of the screw thread is 2.0 mm, and a core diameter is 1.6 mm, and an axial length of the screw is 8.0 mm.

By using a material before forging (homogeneous composite) of the HA/PLLA (HA content 30 wt %), a nail having a head diameter of 3.5 mm, a thickness of 2.0 mm, a diameter of the nail part of 2.5 mm, and a length of 7.0 mm was produced by heat-molding at a temperature of the melting point or higher. On the other hand, a nail similar to that was produced by using the layer-separated composite of the present invention [Layer-separated composite of Sample No. 5 in the aforementioned Table 1 (PLLA:HA/PLLA=15:100, HA content 30 wt %)].

A trial to produce the mini screw was subject to the pressurized forging by scorching those nails into the aforementioned die along with the pitch of the spiral groove of the screw while rotating and moving in the inching operation. Since the former material (homogeneous composite) was poor in flexibility and was hard to be deformed, the material stopped its movement at the entrance of the die during compression, and thus the molding could not be finished. Even if lubrication treatment was carried out to the inner surface of the die, almost no complete article was obtained. This may be due to a factor that the HA fine particles filled homogeneously all over acted in the similar manner as the work hardening. To the contrary, in case of the latter layer-separated composite, when using the lubrication treated die, a molding was smoothly carried out, and a yield which is a success percentage was about 95% or more. The torque strength thereof was the same as or more than the value mentioned in a document [Biomaterials 20 (1999)859-877] where the former forging-reinforced rod was finished by cutting.

Further a nail was produced in the same manner by using the PLLA alone, and the nail was forced to be scorched from its tail end into the die by rotating and moving in the inching operation. However, since the nail made of PLLA alone was not filled with the filler, that is, no toughness, even if the pressure was generated by rotating and moving in the inching operation, the material was softened by pressure. As a result, the pressure could not be transmitted forward, the nail did not go any more and inter into the die.

Example 4

The test of strength was carried out as fundamental property.

A rod of standard size made of the forging-reinforced layer-separated composite produced in the same manner as in Example 1, and the strength thereof was measured according to the following JIS Standard. The result was compared with those of the forged rods of the usual PLLA and HA/PLLA (C1 to C5: Usual products as control). The measurement standards are approximately in the followings.

(Measurement Standard)
Bending Strength (Sb)
  JIS K 7203, Sample size: 3.2 mm diameter, 30 mm length
Tensile Strength (St)
  JIS K 7113, Sample size; 3.2 mm diameter, 50 mm length
Compression Strength (Sc)
  JIS K 7208, Sample size; 5.3 mm diameter, 20 mm length
Impact Strength (Si)
  JIS K 7110, Sample size: 2×12.7×64 mm
Vickers Hardness (Hv)
  Sample size; 10×10×5 mm
Share Strength (Ss)
  Surronen's method mentioned in the document [Biomaterials 20 (2000) 3197-3211], Sample size; 3.2 mm diameter, 30 mm length
Torsional Strength (Ts)
  Torque tester-TEN (Shimpo Industrial Co., Ltd.), Sample size; 3.2 mm diameter, 30 mm length The materials used were as follows.
(1) Control
  C1: PLLA
  C2: HA/PLLA (HA content 20 wt %)
  C3: HA/PLLA (HA content 30 wt %)
  C4: HA/PLLA (HA content 40 wt %)
  C5: HA/PLLA (HA content 50 wt %)
(2) The Forging-Reinforced Layer-Separated Composite of the Present Invention There were used the forging-reinforced layer-separated composites of Sample Nos. 1, 2, 3, 5, 6, 9, 10, 11, 13, 15, 17, 19 mentioned in Table 1 and Table 2 and the forging-reinforced layer-separated composites of the following Sample Nos. 21, 22.

Sample No. 21 is the forging-reinforced layer-separated composite of the same composition as of Sample No. 5, but Sample No. 21 is different from the other samples and controls C1 to C5 in view point of the deformation ratio r value, that is, Sample No. 21 has a r value of 3.2 whereas the others have a deformation ratio r of 2.8. Sample No. 22 is a composite where ½ of the crystalline PLLA of Sample No. 17 is replaced by the non-crystalline PDLLA (D/L=50/50).

The results of the measurement are shown in the following Table.

TABLE 3

Comparison of Properties

| No. | Composition | Bending strength (MPa) | Tensile strength (MPa) | Compression strength (MPa) | Share strength (MPa) | Torsional strength (kg · cm) | Impact strength (kj/cm$^2$) | Hardness |
|---|---|---|---|---|---|---|---|---|
| C1 | PLLA | 258 | 154 | 123 | 93 | 6.6 | 76 | 20 |
| C2 | HA/PLLA (20 wt %) | 252 | 152 | 114 | 127 | 6.8 | — | 20 |
| C3 | HA/PLLA (30 wt %) | 269 | 121 | 106 | 126 | 6.6 | 116 | 22 |
| C4 | HA/PLLA (40 wt %) | 270 | 110 | 107 | 126 | 6.0 | 90 | 23 |
| C5 | HA/PLLA (50 wt %) | 267 | 103 | 115 | 143 | 4.0 | 30 | 26 |
| 1 | [PLLA/HA/PLLA (31.5 wt %) = 5/100]; Total = 30 wt % | 265 | 136 | 114 | 126 | 6.5 | 105 | 22 |

TABLE 3-continued

Comparison of Properties

| No. | Composition | Bending strength (MPa) | Tensile strength (MPa) | Compression strength (MPa) | Share strength (MPa) | Torsional strength (kg·cm) | Impact strength (kj/cm²) | Hardness |
|---|---|---|---|---|---|---|---|---|
| 2 | [PLLA/HA/PLLA (30 wt %) = 5/105]; Total = 28.6 wt % | 265 | 135 | 113 | 126 | 6.4 | 102 | 22 |
| 3 | [PLLA/HA/PLLA (33.0 wt %) = 10/100]; Total = 30 wt % | 260 | 135 | 115 | 120 | 6.7 | — | 22 |
| 5 | [PLLA/HA/PLLA (34.5 wt %) = 15/100]; Total = 30 wt % | 267 | 145 | 118 | 125 | 6.8 | — | 23 |
| 6 | [PLLA/HA/PLLA (30 wt %) = 15/115]; Total = 26.0 wt % | 261 | 151 | 117 | 126 | 6.6 | — | 22 |
| 9 | [PLLA/HA/PLLA (39.0 wt %) = 30/130]; Total = 30 wt % | 265 | 140 | 116 | 123 | 6.3 | — | 23 |
| 10 | [PLLA/HA/PLLA (30 wt %) = 30/130]; Total = 23.0 wt % | 250 | 152 | 114 | 103 | 6.7 | — | 20 |
| 11 | [PLLA/HA/PLLA (42.0 wt %) = 5/100]; Total = 40 wt % | 270 | 110 | 108 | 125 | 6.1 | — | 23 |
| 13 | [PLLA/HA/PLLA (44.0 wt %) = 10/100]; Total = 40 wt % | 268 | 145 | 116 | 123 | 6.5 | — | 25 |
| 15 | [PLLA/HA/PLLA (46.0 wt %) = 15/100]; Total = 40 wt % | 270 | 142 | 116 | 124 | 6.4 | — | 25 |
| 17 | [PLLA/HA/PLLA (48.0 wt %) = 20/100]; Total = 40 wt % | 272 | 137 | 117 | 128 | 6.1 | — | 25 |
| 19 | [PLLA/HA/PLLA (52.0 wt % = 30/130]; Total = 40 wt % | 271 | 151 | 118 | 126 | 6.0 | — | 24 |
| 21 | [PLLA/HA/PLLA (34.5 wt %) = 15/100]; Total = 30 wt %, r = 3.2 | 285 | 140 | 120 | 129 | 6.9 | — | 25 |
| 22 | [PDLLA/PLLA/HA/PLLA (48.0 wt %) = 10/10/100]; Total = 40 wt % | 270 | 140 | 116 | 123 | 6.5 | — | 24 |

As shown in Table 3, values of the inherent strengths of the standard articles which were produced by forging-reinforcing the conventional PLLA-only or the HA/PLLA composites (C2 to C5) where the HA fine particles were added and dispersed to the PLLA in an amount of 20 wt % to 50 wt % at a deformation ratio r=2.8 have the following ranges.

Bending strength (Sb)=258 to 270 MPa, Tensile strength (St)=103 to 154 MPa, Compression strength (Sc)=106 to 123 MPa, Share strength (Ss)=93 to 143 MPa, Torsional strength (Ts)=4.0 to 6.8 Kg·cm, Impact strength (Si)=30 to 116 kj/cm², Vickers hardness (Hv)=20 to 26.

These results show the fact that, in general, the hardness and stiffness were increased by the amount of the HA to be filled, but the extensibility and flexibility were lost.

According to the forging-reinforced composite where the both components are included in the layer-separated state as of the present invention, it was confirmed that the disadvantages of the both could be reinforced complementarily. Namely, it was proved that the reinforced substance had the antinomy properties of the hardness and stiffness and the extensibility and flexibility in good valance.

The layer-separated composite of the present invention can be forged at the deformation ratio r=3.2 as shown in the composite of Sample No. 21, because the moldability of the composite at Tc was increased, which results in relative improvement of strength of the properties. Though the layer-separated composite of Sample No. 22 was one where ½ of the crystalline PLLA of Sample No. 17 is replaced by the non-crystalline PDLLA (D/L=50/50), there was less change in apparent properties between them. However, in practice, since the softness and flexibility were increased a little, the deformation faculty at room temperature in surgical operation could be improved, and since the biodegradation rate of the PDLLA is faster than that of the PLLA and the degraded product accelerates the degradation of the whole components, there is an advantage that disappearance could be achieved early.

Example 5

The test for comparing the toughness of the materials was conducted according to the repetitive bending test by using the mini plate for dental surgery.

The upper surface of a mini screw of Leibinger type of 1.6 mm thickness was pressed by a cross head bar at a rate of 20 mm/min. and when a crossing angle of the cross head bar and the plate was 75 degrees, the plate was reversed. By repeating this procedure, the decrease of the strength and occurrence of breakage were determined. As a result, with respect to the mini plate reinforced by twice forging of the HA/PLLA homogeneous composite, the strength was drastically reduced along with the MD direction at the first forging at about 30 times, and the plate was broken at 44 times. To the contrary, with respect to the mini plate of the layer-separated composite reinforced by twice forging according to the present invention, the strength was reduced a little at about 60 times, and the plate was broken at more than 80 times. Along with the TD direction and DD direction, the reduction of strength and breakage were not observed until the same times as the above, and there was almost no tendency of the lamellar delamination among layers. This is caused from the fact that, according to the forging-reinforced layer-separated composite of the present invention, the layers which are completely fused to each other at the interface form the fine layer-separated structure where the layers are dispersed to any parts of the molded material in the three-dimensionally intermingled state. It seems that, when each fiber layer which composes a matrix where the layer is three-dimensionally intermingled in any direction is deformed by the pressure due to forging, the crystals in the crystalline phase orient disorderly in any direction without anisotropy according to the manner thereof, and as a result, the inherent properties of each material are increased to reinforce the whole properties of the present composite complementarily. Namely, it seems that since the crystal axes of the crystals in the crystalline phase in each separated layer are not oriented in the determined direction uniformly, and the layer is composed of the crystalline phase which is arranged disorderly in any direction without anisotropy, the complementary reinforcement at the interface can be established due to the effect that the mass of the crystals is finely divided by the forging. As a result, it has been confirmed that the fatigue resistance to defying repetitive bending was improved. Since the limit of the bending angle at normal temperature in the conventional case was 120 degrees and, in case of the present invention, was 100 degrees, the present composite could bend at a sharp angle and could not almost cleave and lamellar delamination among layers at the outer surface of the bended point. From the above facts, it has been proved that according to the present invention the forging-reinforced composite is remarkably improved and reinforced in its toughness of dynamic strength such as durability during repeated use.

INDUSTRIAL APPLICABILITY

Since the forging-reinforced composite according to the present invention is enhanced in its various toughness such as tenacity, ductility, malleability or resistance to repeated load by reinforcing the disadvantages of properties of each Layer-separated layer complementarily, it can be utilized suitably various uses where toughness is required such as high strength medical bone fixation and joint devices, and the like.

The invention claimed is:

1. A forging-reinforced composite which is a composite comprising a plural of compatible hetero-componential materials having a polymer comprising a crystalline phase and glass phase at room temperature as a matrix, wherein the compatible hetero-componential materials comprise a first material comprising the matrix polymer and a second material comprising said matrix polymer filled with inorganic fine particles are at least included, wherein said matrix polymer comprising a crystalline phase and glass phase at room temperature is a crystalline poly (lactic acid), and said first material comprises crystalline poly (lactic acid), and said second material comprises crystalline poly (lactic acid) filled with bioceramic fine particles, each of said first material and said second material forms micron-sized fibrous layers, wherein each of said layers has a thickness of from one micron meter to one thousand micron meters, and these micron-sized fibrous layers are welded so as to form a dense block without cavity having a layer-separation state that said layers are three-dimensionally crossed and entangled with each other, whereby inherent properties of each of said layers formed of said first material and said second material, respectively, are reinforced complementarily.

2. The forging-reinforced composite of claim 1, wherein axes of the crystals in the crystalline phase of each of said layers are not oriented in an orderly direction but are disorderly oriented in undetermined directions without anisotropy.

3. The forging-reinforced composite of claim 1, wherein said first material and/or said second material further comprises a non-crystalline poly (lactic acid).

4. The forging-reinforced composite of claim 1, wherein inter surfaces of the micron-sized fibrous layers of the first material and the second material are melted so as to be integrated.

* * * * *